United States Patent
Heiges et al.

(10) Patent No.: US 8,137,384 B2
(45) Date of Patent: Mar. 20, 2012

(54) MODULAR PEDICLE SCREW SYSTEM

(75) Inventors: Bradley A. Heiges, Savannah, GA (US); David E. Lane, II, Lawrenceville, GA (US)

(73) Assignee: BHDL Holdings, LLC, Lawrenceville, GA (US)

( * ) Notice: Subject to any disclaimer, the term of this patent is extended or adjusted under 35 U.S.C. 154(b) by 735 days.

(21) Appl. No.: 12/202,802

(22) Filed: Sep. 2, 2008

(65) Prior Publication Data

US 2010/0057135 A1    Mar. 4, 2010

(51) Int. Cl.
*A61F 2/30* (2006.01)

(52) U.S. Cl. ........................................ 606/254

(58) Field of Classification Search .......... 606/246, 606/254, 257, 265, 266, 279, 287; 623/17.11–17.16
See application file for complete search history.

(56) References Cited

U.S. PATENT DOCUMENTS

| | | | |
|---|---|---|---|
| 2003/0191470 A1* | 10/2003 | Ritland | 606/61 |
| 2004/0172022 A1 | 9/2004 | Landry et al. | |
| 2004/0225289 A1 | 11/2004 | Biedermann et al. | |
| 2005/0059972 A1 | 3/2005 | Biscup | |
| 2005/0143823 A1 | 6/2005 | Boyd et al. | |
| 2005/0154390 A1* | 7/2005 | Biedermann et al. | 606/61 |
| 2005/0203513 A1 | 9/2005 | Jahng et al. | |
| 2005/0216003 A1 | 9/2005 | Biedermann et al. | |
| 2006/0129147 A1 | 6/2006 | Biedermann et al. | |
| 2006/0129149 A1 | 6/2006 | Iott et al. | |
| 2006/0149244 A1 | 7/2006 | Amrein et al. | |
| 2006/0241593 A1 | 10/2006 | Sherman et al. | |
| 2007/0055236 A1 | 3/2007 | Hudgins et al. | |
| 2007/0093826 A1 | 4/2007 | Hawkes et al. | |
| 2007/0123862 A1* | 5/2007 | Warnick | 606/61 |
| 2007/0233087 A1* | 10/2007 | Schlapfer | 606/61 |
| 2008/0021465 A1 | 1/2008 | Shadduck et al. | |
| 2008/0071273 A1 | 3/2008 | Hawkes et al. | |

FOREIGN PATENT DOCUMENTS

EP    1832241    9/2007
WO    WO2004032726    4/2004

* cited by examiner

*Primary Examiner* — David Isabella
*Assistant Examiner* — Ann Schillinger
(74) *Attorney, Agent, or Firm* — McHale & Slavin, P.A.

(57) ABSTRACT

A modular anchoring device including a threaded shank for anchoring within a vertebra, an intermediate element and a head portion configured to receive and secure a rigid or non-rigid stabilization rod. The threaded shank, the intermediate element and the head portion of the anchoring device are cannulated to permit percutaneous implantation of the device. The intermediate portion is designed to be removable from the threaded shank portion subsequent to implantation of the anchoring device to enable substitution of another intermediate element having different dynamic characteristics.

40 Claims, 6 Drawing Sheets

MODULAR PEDICLE SCREW SYSTEM

FIELD OF THE INVENTION

The present invention relates to dynamic spinal stabilization systems. The invention provides a modular pedicle screw attached to the vertebrae to anchor the stabilization system.

BACKGROUND OF THE INVENTION

The spine is comprised of an intricate system of bones and assorted tissues that supports the body and provides protection of the central nervous system including the spinal cord and associated nerves. Within the spinal column are stacked a plurality of vertebrae separated from one another by an intervertebral disc that dampens and cushions the compressive forces exerted upon the spinal column. Located behind the series of alternating vertebrae and discs is the vertebral canal which contains the spinal cord and other associated nerves.

There are more than twenty vertebrae within the spinal column and they are categorized into one of four classifications: cervical, thoracic, lumbar or sacral. The upper seven vertebrae, including the first seven extending downward from the base of the skull are referred to as the cervical vertebrae. The next twelve extending downward from the cervical vertebrae and known as the thoracic vertebrae. Extending downwardly from the thoracic vertebrae are the five lumbar vertebrae. At the base of the spinal column is the sacral bone which also includes the coccyx. The structural and functional relationship of the vertebrae, discs, muscles, ligaments and nerves enables a healthy normal spinal column to move and articulate freely almost without limitation.

The spinal column is comprised of the vertebral body, the pedicle, the spinous process, the transverse process, the facet, the laminar arch, and the vertebral canal. The vertebral body is the generally cylindrically shaped weight bearing structure of the vertebra. The spinous process extends from the rear portion of the vertebra and the transverse processes extend from each side of each vertebra. Both the spinous process and the transverse process connect muscle tissue and ligaments to the spine. The vertebral canal is formed between the vertebral body and the lamina and houses the spinal cord therein. The pedicle is connected to the vertebral body and supports the lamina.

The spinal column may be subject to numerous abnormalities and disorders which can be caused by trauma, disease, or genetic defect such as ruptured or slipped discs, degenerative disc disease, fractured vertebrae as so forth. Such defects can result in conditions causing extreme pain a reduced or abnormal nerve function. These spinal abnormalities can potentially cause damage the nervous system and in particular the spinal cord and likewise impair the normal freedom of motion of the spinal column.

It is not uncommon to treat such abnormalities surgically by spinal fusion wherein one or more vertebral bodies are fused together. However, spinal fusion may limit the spinal cord's range of motion in rotation and lateral bending. In addition, spinal fusion may increase the stress placed upon non fused adjacent vertebral bodies thereby diminishing their structural integrity. Moreover, the fusion device or material may become dislodged move away from the area of implantation.

A wide variety of approaches have been in use to achieve spinal fusion by implanting artificial devices in or on the spinal column to result in immobilization. One approach utilizes an anterior implant where the implant is located on the anterior, or front portion, of the vertebral body. An anterior stabilization can include full or partial disc replacement by a rigid spacer that is approximately the size of the disc that has been removed. A different approach involves the utilization of a posterior implant. Posterior implants include rods that are attached to either the lamina or transverse process by hooks or by pedicle screws. Other posterior implants allow for flexible or dynamic stabilization using pedicle screws connected by rigid or flexible rod member. Prior art posterior pedicle screw based stabilization systems create forces that are often transferred to the anchored pedicle screws. Patients having a relatively brittle bone structure cannot withstand the magnitude of these forces without resulting in the failure of the anchoring system.

DESCRIPTION OF THE PRIOR ART

One example of a dynamic anchoring device is disclosed in US Patent Application Publication 2004/0025289 by Biedermann et al. The device includes an element for anchoring in a bone or vertebra and a head connected to the shank, a receiving part for receiving the head, and a pressure element acting on the head, wherein the pressure element is resilient so that upon a movement of the element from a first angular position of the shank relative to said receiving part into a second angular position the pressure element exerts a return force onto the head to urge the element towards the first angular position.

Another example of a dynamic anchoring device is disclosed in US Patent Application Publication 2005/014823 to Boyd et al. The dynamic stabilization system disclosed therein includes bone anchors having a flexible portion between the bone engaging and head portions of the anchor.

U.S. Patent Application Publication 2005/0216003 to Biedermann et al discloses a bone anchoring element such as a screw. The screw has a shaft and a first head. A second head is elastically connected to the first head. The second head is arranged in the receiving member such that the second head can pivot or swivel. The second head is fixed in the resting member in an angular resting position. The screw is deflectable from the angular head position relative to the second head. The second head is elastically connected to the first head such that a restoring force returns the screw to the angular resting position. The resting angular position of the shaft relative to the receiving part is adjustable.

U.S. Patent Application Publication 2006/0129147 to Biedermann et al discloses a stabilization device for bones or vertebrae that comprises a substantially cylindrical elastic element. The elastic element has a first end and a second end opposite to the first end. An elastic section extends between the first end and the second end. The elastic section includes at least first and second helical coils. The first and second helical coils are arranged coaxially so that the first helical coil extends at least in a portion between the second helical coil. The elastic element may form, for example, a portion of a rod, bone anchoring element, or plate.

U.S. Patent Application Publication 2007/0055236 to Hudgins et al discloses an apparatus and method for stabilizing the facet joints of the spine. The facet implant may be in the form of a screw or other anchor with the intermediate portion in the form of a polyaxial head, a cord a spring, etc.

Another device for the dynamic fixation of impaired spinal column segments in disclosed in U.S. Published Patent Application 2007/0233087 to Schlapfer. The device includes an intermediate element for a detachable, lockable, ball joint like connection having an outer wall concentric with the longitudinal axis and an inner wall forming a coaxial cavity. Either the outer wall or the inner wall comprises one of two contact zones that form the ball joint like connection. The intermediate element is at least partly made of a super elastic material.

U.S. Published Patent Application 2008/0021465 to Shadduck et al discloses a spine implant device for fusion or dynamic stabilization of a spine segment that includes a fixation device with a shaft portion for engaging bone and a proximal end for coupling to a rod that allows for limited flexing of the proximal end relative to the shaft portion.

A further example of a dynamic spinal stabilization system is disclosed in US Published Patent Application 2008/0071273 to Hawkes et al. Disclosed is a system for stabilizing at least one spinal motion segment that includes a fastener having an anchoring portion and a coupling portion and a longitudinal support member couple to the fastener wherein a portion of the system is formed from a super-elastic material.

SUMMARY OF THE INVENTION

The present invention relates to a spinal stabilization system that provides for dynamic stabilization using a modular screw in conjunction with a rigid or non-rigid rod that permits load transfer at the pedicle screw rod interface as opposed to the dynamic rod per se. The screw has an elastic segment interposed between a threaded portion of the screw and the screw head portion, also referred to as a "tulip". The amount or degree of motion can be varied based on the rigidity or flexibility of the elastic material as well as the length and diameter of the elastic material. The pedicle screw is designed to be used in a percutaneous dynamic spinal stabilization system. The screw can be used in a single or multi level construct in combination with a titanium, PEEK or Nitinol rod. The dynamic screw design enables percutaneous delivery of the stabilization system although the dynamic system can be used in an open application as well.

The dynamic spinal stabilization system includes a dynamic modular pedicle screw system which in turn preserves motion in the posterior column of the human spine. The dynamic screws can be used in conjunction with a rigid or non-rigid rod. The dynamic pedicle screw used with a rigid rod will allow for the load transfer to occur at the screw/rod interface as opposed to a non-physiologic load transferred through a dynamic rod alone. Alternatively, the modular pedicle screw can include a rigid segment interposed between a threaded portion of the screw and the screw head portion, also referred to as a "tulip".

Accordingly, it is a primary objective of the instant invention to provide a semi dynamic spinal stabilization system that allows for variable customization of the elastic member thereby increasing the ability to specifically address a greater number of pathologies.

It is a further objective of the instant invention to provide absorption of the dynamic force transmission within the anchoring screw and not at the bone-screw interface.

It is yet another objective of the instant invention to provide a modular pedicle screw that is designed to be used in a percutaneous dynamic stabilization system.

It is a still further objective of the invention to provide a kit of modular anchoring devices for a dynamic spinal stabilization system. The anchoring device is a three part design including a threaded rigid shank, an intermediate component that is an elastic polymer or rigid material, and a rigid multi-axial tulip. The kit would include a plurality of threaded shanks of varying sizes, a plurality of intermediate portions of varying geometries and rigidities, and a plurality of tulip heads.

It is a further object of the invention to provide an intermediate component that is designed to be removable from the threaded shank portion subsequent to implantation of the pedicle screw should the pathology change thereby necessitating a change in the flexibility of the dynamic system. The ability to change the dynamism of the stabilization system without removing the threaded shank portion allows the surgeon to maintain the original bone purchase in the patient which facilitates the procedure, the healing process and improves the potential for long term success.

Another distinct objective of the system is to provide a more comprehensive yet less invasive method to address more complex spine cases, i.e. spinal deformity cases. Currently, dynamic systems are limited in their applicability and mostly ruled out for use in more complex spine cases. One reason may be due to the limited ability to manipulate the individual spine segments in order to obtain the overall correction/objective. This reinforces a current perception that a more invasive technique is always required. This system may not be applicable in all complex cases however it will be a minimally invasive/percutaneous dynamic screw option for surgeons to consider Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
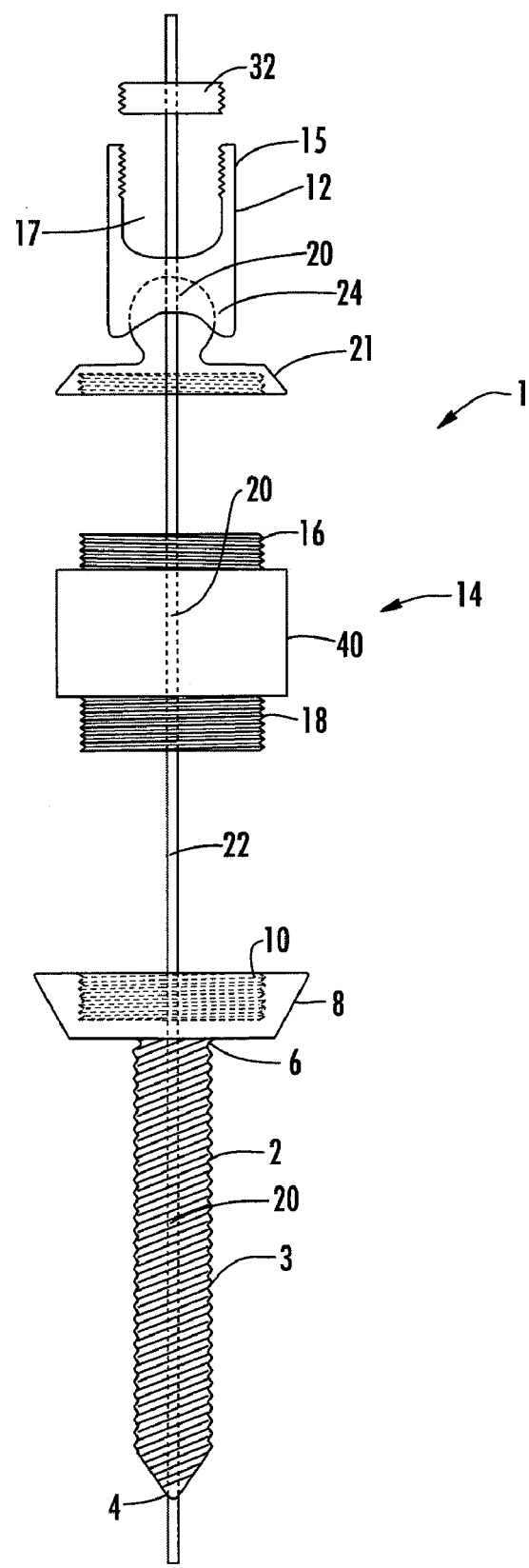
FIG. 1 is a perspective disassembled view of the dynamic modular pedicle screw.
Figure 2:
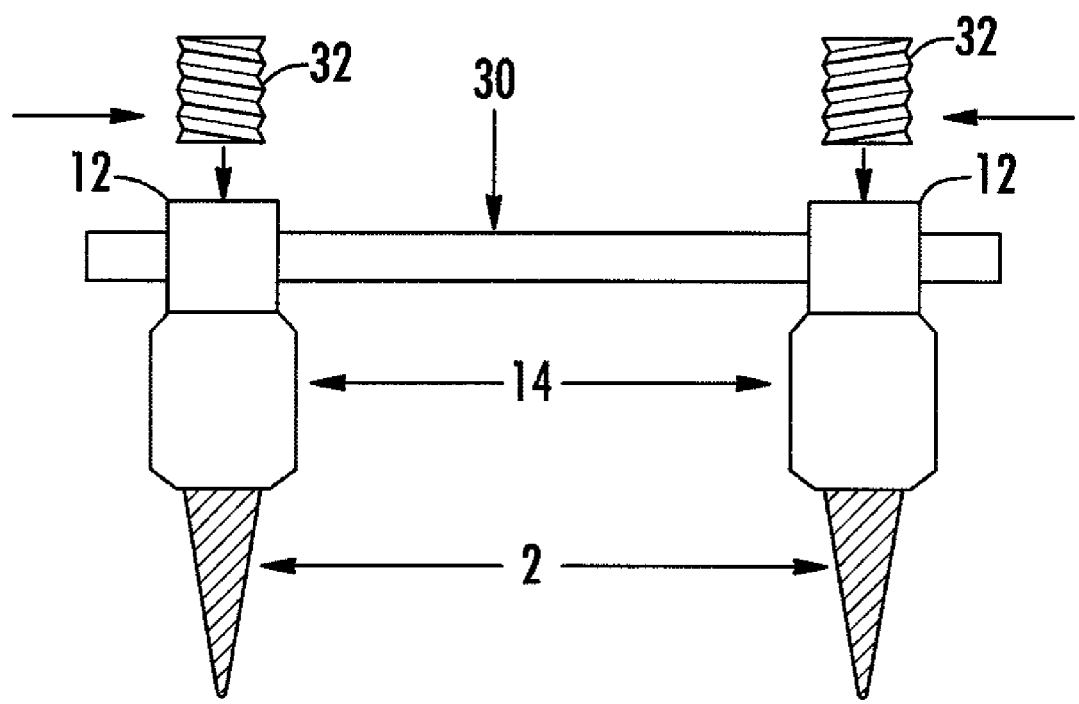
FIG. 2 is a perspective view of the dynamic spine stabilization system showing a multi level construction utilizing a pair of dynamic pedicle screws and a stabilization rod.

FIG. 1 shows a dissembled view of the modular dynamic pedicle screw 1. Screw 1 includes a threaded shank portion 2 having a one end that tapers into a point 4 at one end and has an opposite end 6 that includes a coupling element 8. Coupling element 8 includes internal female threads 10. The pedicle screw 1 has a channel 20 through the entire length of the pedicle screw, including the tulip head 12, the intermediate component 14, and the threaded shank portion 2. This channel 20 allows the pedicle screw 1 to be maneuvered on a Kirschner wire 22, also know as a K-wire. In practice the K-wire is positioned within the patient using fluoroscopy, or other imaging techniques, so as to provide precise positioning of the pedicle screw 1. Once the components are securely positioned the K-wire can be easily removed through the channel 20 which is open at the end of the threaded shank portion and extends through the uppermost portion of the head portion or tulip 12. The threaded shank 2 is externally threaded. The threads 3 can be fenestrated or partially fenestrated. Fenestrated threads are particularly appropriate for osteoporotic patients or patients who require greater assurance of increased pedicle screw purchase based on bone quality. The threaded shank 2 of the pedicle 1 are appropriately sized in relation to the patient's pathology and can be formed in different lengths and external threaded diameters.

The head or tulip portion 12 of the pedicle screw 1 includes upwardly extending cylindrical wall 15 wherein grooves 17 are positioned in diametrically opposed relationship. These opposing grooves 18 allow for top loading of either a rigid or non rigid rod 30 into the tulip. The tulip may be fixed or multi axial. The inner portion of the cylindrical wall accepts a threaded lock screw 32 to secure the rod 30 to the pedicle screw 1. The tulip design can accept tulip extension towers, attached to tulip portion 12, which will facilitate the percutaneous passing of the rod 30 through multiple screws based upon the number of spinal segments involved in the overall dynamic spinal stabilization system. The tulip extensions allow for external control of the tulip head during the rod delivery process. The screw extensions that are attached to the tulip portions remain in place until the percutaneous delivery and placement of the rod 30 has been achieved and threaded lock screws 32 have been finally tightened. In addition, the pedicle screw 1 is also configured to receive a shank extension tower. The screw extension tower is a completely rigid device that extends dorsally through the skin incision. This feature enables three dimensional manipulation of the spine segment. Once the rigid manipulation of the segment is complete the screw extension tower is removed and the dynamic member is fully functional. The tulip design allows for top loading of the rod 30 delivered under direct visualization as is possible when the surgery is performed under open conditions. A coupling element 21 having a cylindrical wall with external threads for engagement with the intermediate member 14 is attached to tulip portion 12 with a ball and socket arrangement 24.

Figure 3A:
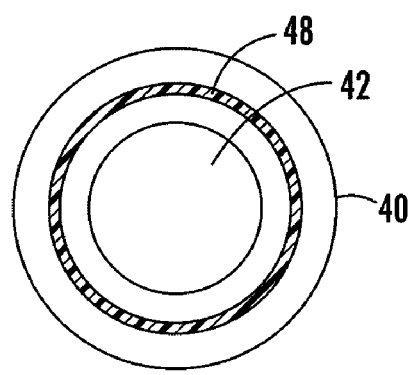
FIG. 3A is a top view of the elastic intermediate member.
Figure 4A:
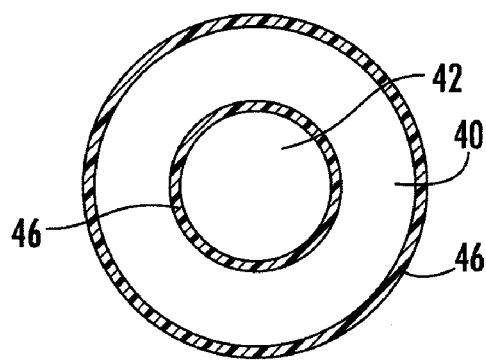
FIG. 4A is a top view of a second embodiment for the elastic intermediate member.
Figure 3B:
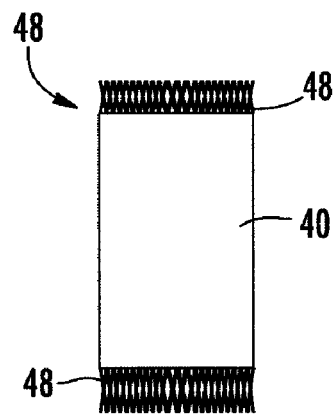
FIG. 3B is a side view of the elastic intermediate member.
Figure 4B:
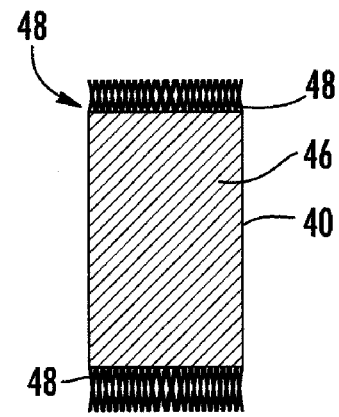
FIG. 4B is a side view of the second embodiment for the elastic intermediate member.
Figure 3C:
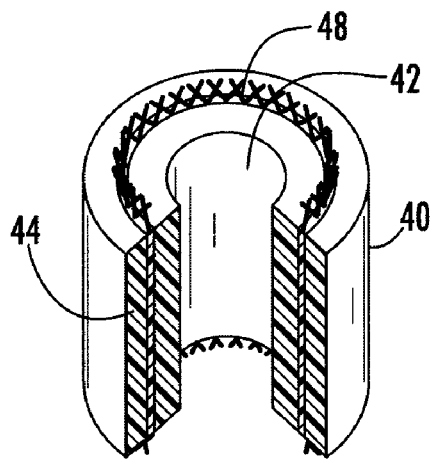
FIG. 3C is a sectional perspective view of the elastic intermediate.
Figure 4C:
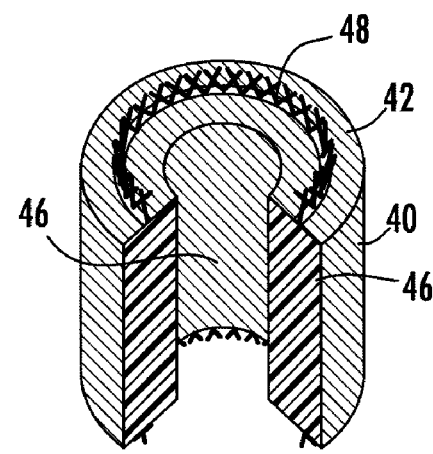
FIG. 4C is a sectional perspective view of the second embodiment for the elastic intermediate member.
Figure 5A:
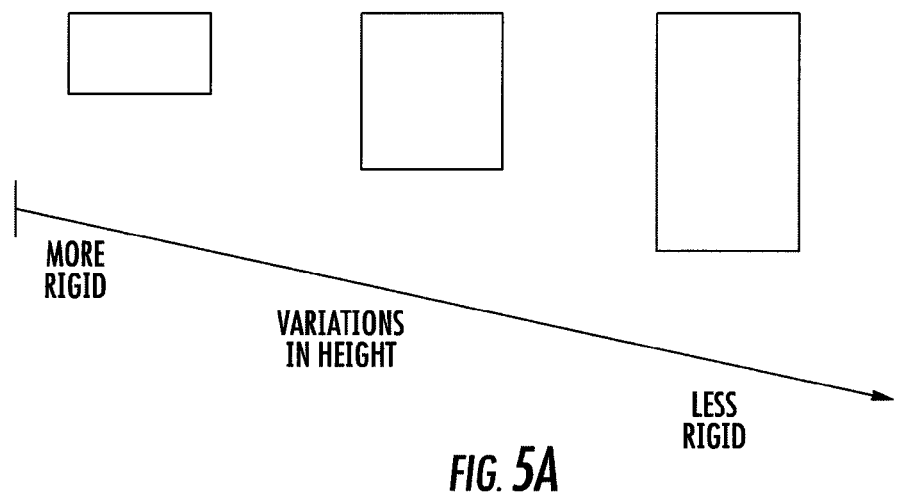
FIGS. 5A and 5B show various configurations for the elastic portion and their relative dynamic properties.
Figure 5B:
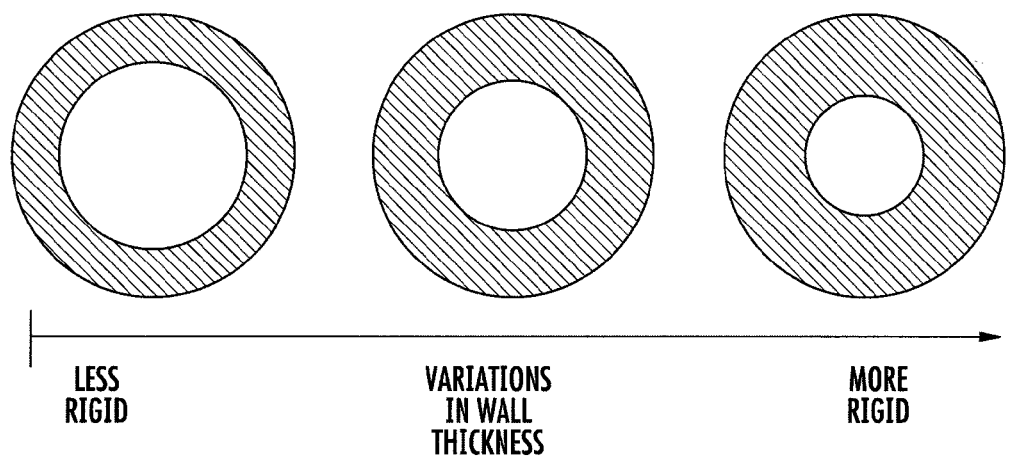

The intermediate portion 14 of the dynamic pedicle screw includes an elastic portion 40, an upper coupling member 16 and a lower coupling member 18. As shown in FIGS. 3A-3C, portion 40 is generally cylindrical in shape and includes a passageway 42 concentric with the longitudinal axis of the cylindrical body. The portion 40 is formed from elastic motion preserving dynamic material which allows for the requisite degree of motion and is capable of standing the mechanical loads associated with the human spine. This provides intraoperative flexibility for the surgeon to choose or customize the construct to address the patient's specific pathology. The portion 40 is available in varying levels, ranges and modes of dynamism, such as dynamic, motion preserving, non-fusion and rigid. Dynamism can be adjusted based on the type of material used, for example Nitinol or polycarbonate, the length of the cylinder, the diameter and or wall thickness of the cylinder or any combination of the above variables (as shown in FIGS. 5A and 5B). Embedded within the wall of cylindrical portion 40 is a jacket 44 made from a polyester material, or the like, which extends outwardly from each end of the cylinder 40, as shown in FIGS. 3A through 3C. A second embodiment, shown in FIGS. 4A through 4C utilizes a polyester, or the like, jacket that surrounds the outer surfaces of cylindrical member 40 and extends outwardly from each end of the cylinder 40. Extending portions 48 of the jacket extend into tabs formed in the upper and lower coupling members, 16 and 18 respectively, to complete the assembly of the intermediate portion 14. Upper coupling member 16 includes a cylindrical wall having an externally threaded surface. Upper coupling member 16 is threadably connected to tulip coupling member 22. Likewise, lower coupling member 18 includes a cylindrical wall having an externally threaded surface. Lower coupling member 18 is screwed on to coupling member 8 positioned on the threaded shank portion 2. As an alternative, cylindrical member 40 can be bonded, glued or molded directly on to the upper and lower coupling members, 16 and 18 respectively, without the utilization of a jacket.

The intermediate portion can also be rigid allowing for rigid fixation. In order to assemble a rigid modular screw a non-elastic intermediate portion 14 is coupled to the threaded shank portion 2 and the tulip head portion 12. In this instance, cylindrical member 40 can be made from the same material as the threaded shank 2 or the tulip head 12 or some other rigid compatible material. The non-elastic cylindrical member 40 can be threaded into upper and lower coupling members or otherwise suitably affixed thereto.

Figure 6A:
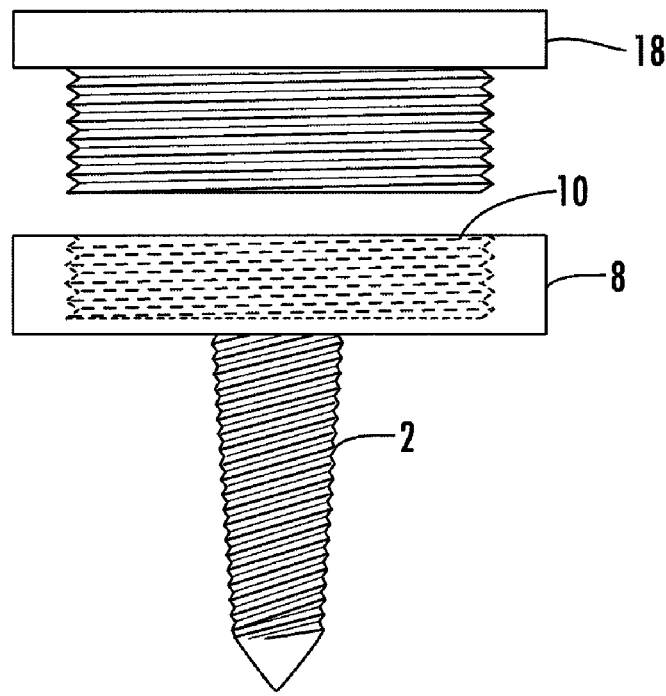
FIG. 6A is an exploded side view of the lower coupling the intermediate member and the threaded shank.
Figure 6B:
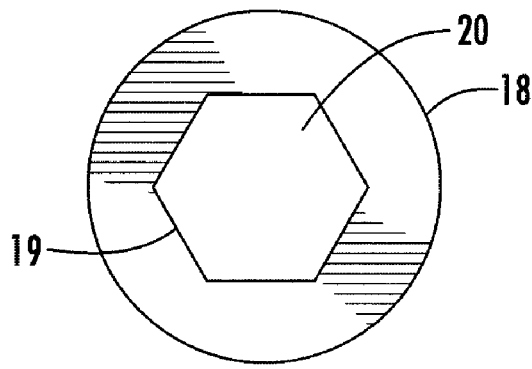
FIG. 6B is a top view of the lower coupling member of the intermediate member.
Figure 6C:
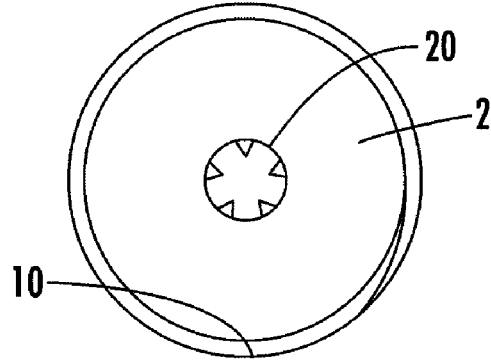
FIG. 6C is a top of view of the threaded shank portion.

FIG. 6A illustrates the lower coupling member 18 and the threaded shank 2 with its coupling member 8. Annular threads 10 on coupling 8 mate with external threads on lower coupling member 18. FIG. 6B is a top view of lower coupling member 18 showing a socket 19 that includes a portion of channel 20. Socket 19 is designed to operatively engage an insertion or removal tool which can be inserted through the intermediate portion 14 via channel 20. Should it be necessary to change the dynamic characteristics of the spinal support system the surgeon would remove the rod 30 from the head 12 by first removing threaded lock screw 32. Following removal of the rod 30 the head portion 12 would be unthreaded from the intermediate portion 14 using an appropriate tool. Thereafter, a tool would be inserted through the channel 20 in the intermediate member 14 to engage socket 19 formed in lower coupling member 18. Upon rotation of the tool the lower coupling 18 of the intermediate member will be unthreaded from the second coupling 8 formed on the threaded shank portion 2. The intermediate portion can then be removed from the patient. A new intermediate portion 14 can then be positioned over the existing threaded shank portion 2. Thereafter a tool would be inserted through channel 20 of the intermediate member 14 and engage socket 19 formed in the lower coupling member 8. Upon rotation of the tool the lower coupling 18 of the intermediate member 14 will be threaded into the second coupling formed on the treaded shank 2. The head portion 12 can then be threaded onto the intermediate portion 14 and the rod 30 can be affixed thereto by locking screw 32. The ability to change the dynamism of the stabilization system without removing the threaded shank portion allows the surgeon to maintain the original bone purchase in the patient which facilitates the procedure, the healing process and improves the potential for long term success. FIG. 6C is a top view of the threaded shank 2 with channel 20 and coupling threads 10.

Figure 7A:
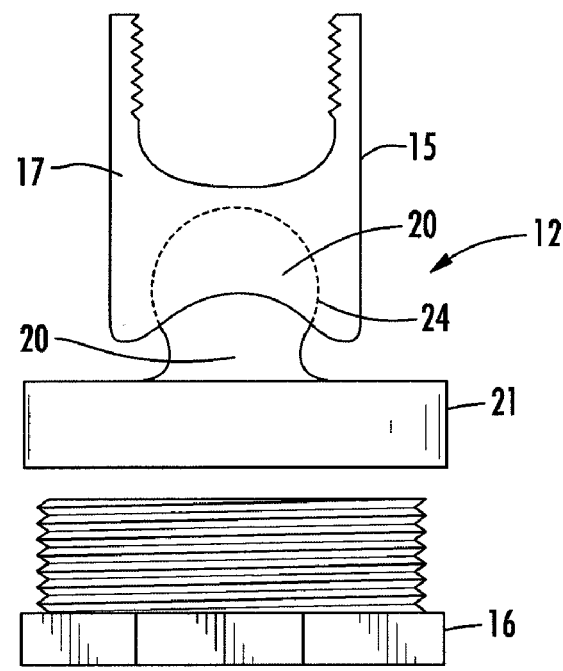
FIG. 7A is a side view of the upper coupling member and the tulip head.
Figure 7B:
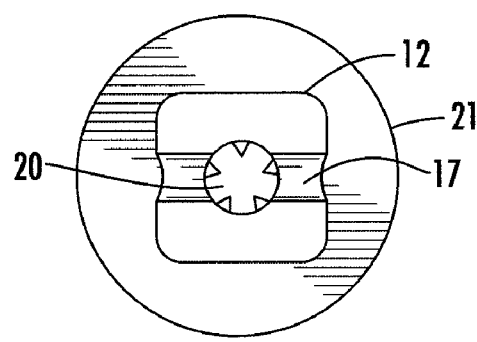
FIG. 7B is a top view of the tulip head component.
Figure 7C:
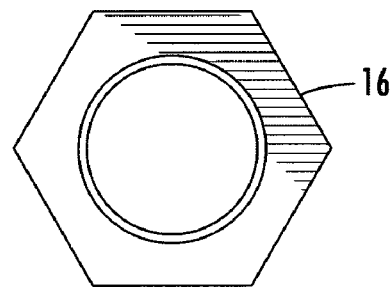
FIG. 7C is a top view of the upper coupling member of the intermediate element.

FIG. 7A is a side view showing tulip head member 12 with cylindrical side walls 15 and groove 17. A coupling element 21 having a cylindrical wall with external threads for engagement with the intermediate member 14 is attached to tulip portion 12 with a ball and socket arrangement 24. FIG. 7B is a side view of tulip head member 12. FIG. 7C is a top view of the upper coupling member 16.

The rod 30 connects multiple screws based upon the number of segments involved in the overall construct. The rod can be of any compatible material (PEEK, Titanium, Nitinol, etc). This also increases the versatility of the system allowing for more control in defining the rigidity or dynamism of the overall construct. The rod 30 used in conjunction with the dynamic pedicle screw system can be either rigid or non rigid.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A modular dynamic pedicle screw system comprising:
   a plurality of modular dynamic pedicle screws and a rod, each modular pedicle screw including a head portion, an intermediate portion, and a threaded shank portion,
   said head portion including a cylindrical wall with diametrically opposed grooves that extend downwards from the top of said cylindrical wall, said grooves are sized and configured to receive said rod within said diametrically opposed grooves, and a lock screw configured to engage threads formed on an inner surface of said cylindrical wall thereby securing said rod to said head portion, said head portion including a first channel formed coincident with its longitudinal axis and open at the top and the bottom of the head portion, and, a first coupling element connected to said head portion,
   said intermediate portion including an elastic portion and an upper coupling member and a lower coupling member, said elastic portion and said upper and lower coupling being fixedly connected, said intermediate portion including a second channel extending coincident with its longitudinal axis and open at the top and bottom of said intermediate member, wherein said elastic portion is generally cylindrical in shape and wherein in the elastic portion further includes a jacket that surrounds the outer surfaces of said cylindrical elastic portion and extends outwardly from the top and bottom ends of the cylinder, the jacket portion extending outward from the top of the cylinder is affixed into tabs located in the upper coupling member and the jacket portion extending outward from the bottom of the cylinder is affixed into tabs formed in the lower coupling member, thereby completing the assembling of the intermediate portion,
   said threaded shank portion including a threaded and tapered outer surface and a second coupling member formed at one end thereof, said threaded shank portion and said second coupling member each having a third channel formed coincident with the longitudinal axis of said threaded shank portion and open at the top and bottom of said threaded shank portion,
   said first, second and third channels are configured to be in alignment with one another,
   whereby a wire can pass freely from the open bottom end of the threaded shank portion, through the intermediate portion, and out the open top end of the head portion and be completely removed from the pedicle screw.

2. The modular dynamic pedicle screw system of claim 1, wherein the first coupling of the head portion is threadably engaged by the upper coupling of the intermediate portion.

3. The modular dynamic pedicle screw system of claim 1, wherein the second coupling of the threaded shank portion is threadably engaged by the lower coupling of the intermediate portion.

4. The modular dynamic pedicle screw system of claim 1 wherein said head portion includes a ball and socket connection between the cylindrical wall portion and the first coupling element.

5. The modular dynamic pedicle screw system of claim 1 wherein said rod is flexible.

6. The modular dynamic pedicle screw system of claim 1 wherein said rod is rigid.

7. The modular dynamic pedicle screw system of claim 1 wherein said lower coupling includes at least one surface that can be engaged by a tool passing through the second channel whereby the intermediate portion can be rotated in either direction causing the lower coupling to be either threaded or unthreaded from the second coupling on the threaded shank.

8. A modular dynamic pedicle screw comprising:
   said modular dynamic pedicle screw including a head portion, an intermediate portion, and a threaded shank portion,
   said head portion including a cylindrical wall with diametrically opposed grooves that extend downwards from the top of said cylindrical wall, said grooves are sized and adapted to receive a rod within said diametrically opposed grooves, and a lock screw configured to engage threads formed on an inner surface of said cylindrical wall thereby securing said rod to said head portion, said head portion including a first channel formed coincident with its longitudinal axis and open at the top and the bottom of the head portion, and, a first coupling element connected to said head portion,
   said intermediate portion including an elastic portion and an upper coupling member and a lower coupling member, said elastic portion and said upper and lower coupling being fixedly connected, said intermediate portion including a second channel extending coincident with its longitudinal axis and open at the top and bottom of said intermediate member, wherein said elastic portion is generally cylindrical in shape and wherein in the elastic portion further includes a jacket that surrounds the outer surfaces of said cylindrical elastic portion and extends outwardly from the top and bottom ends of the cylinder, the jacket portion extending outward from the top of the cylinder is affixed into tabs located in the upper coupling member and the jacket portion extending outward from the bottom of the cylinder is affixed into tabs formed in the lower coupling member, thereby completing the assembling of the intermediate portion, said threaded shank portion including a threaded and tapered outer surface and a second coupling member formed at one end thereof, said threaded shank portion and said second coupling member each having a third channel formed coincident with the longitudinal axis of said threaded shank portion and open at the top and bottom of said threaded shank portion, said first, second and third channels are configured to be in alignment with one another, whereby a wire can pass freely from the open bottom end of the threaded shank portion, through the intermediate portion, and out the open top end of the head portion and be completely removed from the modular dynamic pedicle screw.

9. The modular dynamic pedicle screw of claim 8, wherein the first coupling of the head portion is threadably engaged by the upper coupling of the intermediate portion.

10. The modular dynamic pedicle screw of claim 8, wherein the second coupling of the threaded shank portion is threadably engaged to the lower coupling of the intermediate portion.

11. The modular dynamic screw of claim 8, wherein said head portion includes a ball and socket connection between the cylindrical wall portion and the first coupling element.

12. The modular dynamic screw of claim 8, wherein said lower coupling includes a socket that can be engaged by a tool passing through the second channel whereby the intermediate portion can be rotated in either direction causing the lower coupling to be either threaded or unthreaded from the second coupling on the threaded shank.

13. A modular dynamic pedicle screw system comprising:
a plurality of modular dynamic pedicle screws and a rod, each modular pedicle screw including a head portion, an intermediate portion, and a threaded shank portion, said head portion including a cylindrical wall with diametrically opposed grooves that extend downwards from the top of said cylindrical wall, said grooves are sized and configured to receive said rod within said diametrically opposed grooves, and a lock screw configured to engage threads formed on an inner surface of said cylindrical wall thereby securing said rod to said head portion, said head portion including a first channel formed coincident with its longitudinal axis and open at the top and the bottom of the head portion, and, a first coupling element connected to said head portion, said intermediate portion including an elastic portion and an upper coupling member and a lower coupling member, said elastic portion and said upper and lower coupling being fixedly connected, said intermediate portion including a second channel extending coincident with its longitudinal axis and open at the top and bottom of said intermediate member, wherein said elastic portion is generally cylindrical in shape and wherein in the elastic portion further includes a jacket in imbedded between the outer surfaces of said cylindrical elastic portion and extends outwardly from the top and bottom ends of the cylinder, the jacket portion extending outward from the top of the cylinder is affixed into tabs located in the upper coupling member and the jacket portion extending outward from the bottom of the cylinder is affixed into tabs formed in the lower coupling member, thereby completing the assembling of the intermediate portion, said threaded shank portion including a threaded and tapered outer surface and a second coupling member formed at one end thereof, said threaded shank portion and said second coupling member each having a third channel formed coincident with the longitudinal axis of said threaded shank portion and open at the top and bottom of said threaded shank portion, said first, second and third channels are configured to be in alignment with one another, whereby a wire can pass freely from the open bottom end of the threaded shank portion, through the intermediate portion, and out the open top end of the head portion and be completely removed from the pedicle screw.

14. The modular dynamic pedicle screw system of claim 13, wherein the first coupling of the head portion is threadably engaged by the upper coupling of the intermediate portion.

15. The modular dynamic pedicle screw system of claim 13, wherein the second coupling of the threaded shank portion is threadably engaged by the lower coupling of the intermediate portion.

16. The modular dynamic pedicle screw system of claim 13 wherein said head portion includes a ball and socket connection between the cylindrical wall portion and the first coupling element.

17. The modular dynamic pedicle screw system of claim 13 wherein said rod is flexible.

18. The modular dynamic pedicle screw system of claim 13 wherein said rod is rigid.

19. The modular dynamic pedicle screw system of claim 13 wherein said lower coupling includes at least one surface that can be engaged by a tool passing through the second channel whereby the intermediate portion can be rotated in either direction causing the lower coupling to be either threaded or unthreaded from the second coupling on the threaded shank.

20. A modular dynamic pedicle screw system comprising:
a plurality of modular dynamic pedicle screws and a rod, each modular pedicle screw including a head portion, an intermediate portion, and a threaded shank portion, said head portion including a cylindrical wall with diametrically opposed grooves that extend downwards from the top of said cylindrical wall, said grooves are sized and configured to receive said rod within said diametrically opposed grooves, and a lock screw configured to engage threads formed on an inner surface of said cylindrical wall thereby securing said rod to said head portion, said head portion including a first channel formed coincident with its longitudinal axis and open at the top and the bottom of the head portion, and, a first coupling element connected to said head portion, wherein said head portion includes a ball and socket connection between the cylindrical wall portion and the first coupling element, said intermediate portion including an elastic portion and an upper coupling member and a lower coupling member, said elastic portion and said upper and lower coupling being fixedly connected, said intermediate portion including a second channel extending coincident with its longitudinal axis and open at the top and bottom of said intermediate member, said threaded shank portion including a threaded and tapered outer surface and a second coupling member formed at one end thereof, said threaded shank portion and said second coupling member each having a third channel formed coincident with the longitudinal axis of said threaded shank portion and open at the top and bottom of said threaded shank portion, said first, second and third channels are configured to be in alignment with one another, whereby a wire can pass freely from the open bottom end of the threaded shank portion, through the intermediate portion, and out the open top end of the head portion and be completely removed from the pedicle screw.

21. The modular dynamic pedicle screw system of claim 20, wherein the first coupling of the head portion is threadably engaged by the upper coupling of the intermediate portion.

22. The modular dynamic pedicle screw system of claim 20, wherein the second coupling of the threaded shank portion is threadably engaged by the lower coupling of the intermediate portion.

23. The modular dynamic pedicle screw system of claim 20, wherein said elastic portion is generally cylindrical in shape.

24. The modular dynamic pedicle screw system of claim 23, wherein in the elastic portion further includes a jacket that surrounds the outer surfaces of said cylindrical elastic portion and extends outwardly from the top and bottom ends of the cylinder, the jacket portion extending outward from the top of the cylinder is affixed into tabs located in the upper coupling member and the jacket portion extending outward from the bottom of the cylinder is affixed into tabs formed in the lower coupling member, thereby completing the assembling of the intermediate portion.

25. The modular dynamic pedicle screw system of claim 23, wherein in the elastic portion further includes a jacket in imbedded between the outer surfaces of said cylindrical elastic portion and extends outwardly from the top and bottom ends of the cylinder, the jacket portion extending outward from the top of the cylinder is affixed into tabs located in the upper coupling member and the jacket portion extending outward from the bottom of the cylinder is affixed into tabs formed in the lower coupling member, thereby completing the assembling of the intermediate portion.

26. The modular dynamic pedicle screw system of claim 20 wherein said rod is flexible.

27. The modular dynamic pedicle screw system of claim 20 wherein said rod is rigid.

28. The modular dynamic pedicle screw system of claim 20 wherein said lower coupling includes at least one surface that can be engaged by a tool passing through the second channel whereby the intermediate portion can be rotated in either direction causing the lower coupling to be either threaded or unthreaded from the second coupling on the threaded shank.

29. A modular dynamic pedicle screw comprising: said modular dynamic pedicle screw including a head portion, an intermediate portion, and a threaded shank portion, said head portion including a cylindrical wall with diametrically opposed grooves that extend downwards from the top of said cylindrical wall, said grooves are sized and adapted to receive a rod within said diametrically opposed grooves, and a lock screw configured to engage threads formed on an inner surface of said cylindrical wall thereby securing said rod to said head portion, said head portion including a first channel formed coincident with its longitudinal axis and open at the top and the bottom of the head portion, and, a first coupling element connected to said head portion, said intermediate portion including an elastic portion and an upper coupling member and a lower coupling member, said elastic portion and said upper and lower coupling being fixedly connected, said intermediate portion including a second channel extending coincident with its longitudinal axis and open at the top and bottom of said intermediate member, wherein said elastic portion is generally cylindrical in shape and wherein in the elastic portion further includes a jacket in imbedded between the outer surfaces of said cylindrical elastic portion and extends outwardly from the top and bottom ends of the cylinder, the jacket portion extending outward from the top of the cylinder is affixed into tabs located in the upper coupling member and the jacket portion extending outward from the bottom of the cylinder is affixed into tabs formed in the lower coupling member, thereby completing the assembling of the intermediate portion, said threaded shank portion including a threaded and tapered outer surface and a second coupling member formed at one end thereof, said threaded shank portion and said second coupling member each having a third channel formed coincident with the longitudinal axis of said threaded shank portion and open at the top and bottom of said threaded shank portion, said first, second and third channels are configured to be in alignment with one another, whereby a wire can pass freely from the open bottom end of the threaded shank portion, through the intermediate portion, and out the open top end of the head portion and be completely removed from the modular dynamic pedicle screw.

30. The modular dynamic pedicle screw of claim 29, wherein the first coupling of the head portion is threadably engaged by the upper coupling of the intermediate portion.

31. The modular dynamic pedicle screw of claim 29, wherein the second coupling of the threaded shank portion is threadably engaged to the lower coupling of the intermediate portion.

32. The modular dynamic screw of claim 29, wherein said head portion includes a ball and socket connection between the cylindrical wall portion and the first coupling element.

33. The modular dynamic screw of claim 29, wherein said lower coupling includes a socket that can be engaged by a tool passing through the second channel whereby the intermediate portion can be rotated in either direction causing the lower coupling to be either threaded or unthreaded from the second coupling on the threaded shank.

34. A modular dynamic pedicle screw comprising: said modular dynamic pedicle screw including a head portion, an intermediate portion, and a threaded shank portion, said head portion including a cylindrical wall with diametrically opposed grooves that extend downwards from the top of said cylindrical wall, said grooves are sized and adapted to receive a rod within said diametrically opposed grooves, and a lock screw configured to engage threads formed on an inner surface of said cylindrical wall thereby securing said rod to said head portion, said head portion including a first channel formed coincident with its longitudinal axis and open at the top and the bottom of the head portion, and, a first coupling element connected to said head portion, wherein said head portion includes a ball and socket connection between the cylindrical wall portion and the first coupling element, said intermediate portion including an elastic portion and an upper coupling member and a lower coupling member, said elastic portion and said upper and lower coupling being fixedly connected, said intermediate portion including a second channel extending coincident with its longitudinal axis and open at the top and bottom of said intermediate member, said threaded shank portion including a threaded and tapered outer surface and a second coupling member formed at one end thereof, said threaded shank portion and said second coupling member each having a third channel formed coincident with the longitudinal axis of said threaded shank portion and open at the top and bottom of said threaded shank portion, said first, second and third channels are configured to be in alignment with one another, whereby a wire can pass freely from the open bottom end of the threaded shank portion, through the intermediate portion, and out the open top end of the head portion and be completely removed from the modular dynamic pedicle screw.

35. The modular dynamic pedicle screw of claim 34, wherein the first coupling of the head portion is threadably engaged by the upper coupling of the intermediate portion.

36. The modular dynamic pedicle screw of claim 34, wherein the second coupling of the threaded shank portion is threadably engaged to the lower coupling of the intermediate portion.

37. The modular dynamic pedicle screw of claim 34, wherein said elastic portion is generally cylindrical in shape.

38. The modular dynamic pedicle screw of claim 37, wherein in the elastic portion further includes a jacket that surrounds the outer surfaces of said cylindrical elastic portion and extends outwardly from the top and bottom ends of the cylinder, the jacket portion extending outward from the top of the cylinder is affixed into tabs located in the upper coupling member and the jacket portion extending outward from the bottom of the cylinder is affixed into tabs formed in the lower coupling member, thereby completing the assembling of the intermediate portion.

39. The modular dynamic pedicle screw of claim 37, wherein in the elastic portion further includes a jacket in imbedded between the outer surfaces of said cylindrical elastic portion and extends outwardly from the top and bottom ends of the cylinder, the jacket portion extending outward from the top of the cylinder is affixed into tabs located in the upper coupling member and the jacket portion extending outward from the bottom of the cylinder is affixed into tabs formed in the lower coupling member, thereby completing the assembling of the intermediate portion.

40. The modular dynamic screw of claim 34, wherein said lower coupling includes a socket that can be engaged by a tool passing through the second channel whereby the intermediate portion can be rotated in either direction causing the lower coupling to be either threaded or unthreaded from the second coupling on the threaded shank.

\* \* \* \* \*